(12) United States Patent
Zinth et al.

(10) Patent No.: US 7,886,579 B2
(45) Date of Patent: Feb. 15, 2011

(54) PORTABLE SAMPLER

(75) Inventors: Peter Zinth, Buchenberg (DE);
Wolfgang Steidle, Kempten (DE);
Tobias Stuckl, Kempten (DE)

(73) Assignee: Endress + Hauser Wetzer GmbH + Co. KG, Nesselwang (DE)

( * ) Notice: Subject to any disclaimer, the term of this patent is extended or adjusted under 35 U.S.C. 154(b) by 549 days.

(21) Appl. No.: 10/960,688

(22) Filed: Oct. 8, 2004

(65) Prior Publication Data

US 2005/0150567 A1    Jul. 14, 2005

Related U.S. Application Data

(60) Provisional application No. 60/529,626, filed on Dec. 16, 2003.

(30) Foreign Application Priority Data

Oct. 9, 2003    (DE) .................................. 10347626

(51) Int. Cl.
*G01N 9/00* (2006.01)
*B65B 43/42* (2006.01)
(52) U.S. Cl. ..................... 73/31.05; 141/130
(58) Field of Classification Search ............. 417/477.1, 417/477.8, 477.9; 141/284, 130; 73/31.05, 73/863.01, 863.02, 863.11, 863.33, 863.31, 73/864, 864.34, 864.35
See application file for complete search history.

(56) References Cited

U.S. PATENT DOCUMENTS

| 3,971,877 | A | * | 7/1976 | Lee ........................... 174/16.1 |
| 4,083,226 | A | | 4/1978 | Eckstein |
| 5,043,617 | A | * | 8/1991 | Rostron ...................... 310/112 |
| 5,096,385 | A | * | 3/1992 | Georgi et al. ................. 417/18 |
| 5,340,543 | A | * | 8/1994 | Annino et al. ................ 422/89 |
| 5,915,932 | A | * | 6/1999 | Nabity et al. ............. 417/477.1 |
| 6,354,345 | B1 | | 3/2002 | Nabity |
| 6,871,551 | B2 | * | 3/2005 | Beller et al. .................. 73/861 |
| 2002/0001527 | A1 | * | 1/2002 | Beller et al. ................ 417/300 |
| 2003/0136700 | A1 | * | 7/2003 | Zeller ...................... 206/524.4 |

FOREIGN PATENT DOCUMENTS

| DE | 28 24 153 A1 | 12/1979 |
| DE | 297 22 468 U1 | 5/1998 |
| DE | 102 52 158 A1 | 7/2003 |
| WO | WO 92/08963 | 5/1992 |

OTHER PUBLICATIONS

XP-002316557, Isco 3780 Product Data, 2002.
XP-002316558, Isco 3780 Zone 1 Rated Sampler, Instruction Manual, 2002.

* cited by examiner

*Primary Examiner*—John Fitzgerald
(74) *Attorney, Agent, or Firm*—Bacon & Thomas, PLLC

(57) ABSTRACT

A portable sampler for use in an explosion-endangered area, having a housing, in which at least the following components are arranged: a pump unit having a first drive unit, a sensor for determining the amount of sample supplied from the pump unit, a control unit, which controls the taking of a desired amount of sample and the filling thereof into at least one container, and at least one power supply unit, which provides the power for driving the first drive unit, the sensor and the control unit, The following components: the control unit, the power supply unit, the first drive unit and the sensor, are modularly constructed, and each such module is embodied such that it satisfies a specified ignition protection type.

13 Claims, 2 Drawing Sheets

PORTABLE SAMPLER

This application claims the benefit of provisional application No. 60/529,626 filed Dec. 16, 2003.

FIELD OF THE INVENTION

The invention relates to a portable sampler having a housing, in which at least the following components are arranged: A pump having a first drive unit, a sensor for determining the amount of sample supplied by the pump, a control unit, which controls the taking of a desired amount of sample and the filling thereof into at least one container, and at least one energy storage unit, which provides the power for operating the drive unit, the sensor, and the control unit.

BACKGROUND OF THE INVENTION

Samplers of this kind are described, for example, in DE-U 297 22 468, DE-A 102 52 158, DE-A 28 24 153, WO-A 95/02176 and U.S. Pat. No. 4,415,011 and are available from the assignee under the names LIQUI-PORT and LIQUI-BOX. Especially the sampler described in DE-U 297 22 468 is also provided for application in an explosion-endangered area.

Special safety requirements are placed on devices usable in explosion-endangered areas. These requirements have the goal of avoiding the creation of sparks, which, under the right conditions, could trigger an explosion, or of preventing that a spark occurring inside a closed space results in effects on the surroundings. This goal is achievable in various ways referenced in corresponding European standards as ignition protection types. Thus, e.g., according to European Standard EN 50 020 dated 1994, explosion protection is present, when devices are constructed according to the protection class defined therein with the name 'Intrinsic Safety' (EEx 'ib'). According to this protection class, the values for the electrical variables current, voltage, converted, respectively convertible, power, and stored or storable energy in a device must lie, at all times, below specified limit values. The limit values are selected such that, in case of a malfunction, e.g. a short circuit, the maximum resulting heat is not sufficient to produce an ignition spark. The current is e.g. held within specified limit values by resistances, the voltages e.g. by Zener diodes, and the power by corresponding combinations of current and voltage limiting components. The European Standard EN 50 019 dated 1994 specifies a further protection class with the name "Extended Safety" (EEx 'e'). In the case of devices, which are constructed according to this protection class, the explosion protection is achieved by providing spatial separations between two different electric potentials sufficiently great that a spark formation is prevented by distance in the case of malfunction. This can, however, lead in certain circumstances to the necessity for very large dimensions, in order to satisfy these conditions. A further protection class bearing the designation "Pressure-Tight Encapsulation" (EEx 'd') is described in the European Standard EN 50 018 dated 1994. Devices which are constructed according to this protection class have a pressure-tight housing, which assures that an explosion occurring in the interior of the housing cannot be transmitted to the exterior. Pressure-tight housings are thick-walled, in order to have a sufficient mechanical strength, and are consequently heavy and expensive. The USA, Canada, Japan and other countries have standards which are comparable with these European standards.

The sampler described in DE-U 297 22 468 is, for the purpose of assuring a sufficient explosion safety, provided with an explosion protection device supplied by an auxiliary, current and compressed air supply, with practically all electrical components of the sampler being accommodated in the single, explosion-secured housing. However, a disadvantage of this explosion protection device can be seen in that this current and compressed air supply can itself potentially fail, in which case, in turn, the explosion protection for the entire sampler is terminated unexpectedly and suddenly. A further disadvantage of this sampler is that the auxiliary current and compressed air supply also effects a considerable increase in the weight of the sampler, which, in turn, degrades portability considerably.

SUMMARY OF THE INVENTION

An object of the invention is to provide a sampler, which is as light as possible, especially portable and easily manageable manually, for application in an explosion-endangered area.

The object is achieved by providing that components of the sampler, such as e.g. a pump unit with a first drive unit, a sensor for determining the sample amount supplied by the pump unit, a control unit that controls the taking of a desired amount of sample and the filling thereof into at least one container, a power supply unit that supplies the energy for operating the first drive unit, the sensor and the control unit, or the like, are modularly constructed and that each of these modules is embodied such that it satisfies a specified type of ignition protection. The types of ignition protection can be matched individually, optimally to the special requirements of the particular components. The sampler is, in this way, suited for application in an explosion-endangered area. Due to the relatively small weight, the sampler of the invention can be transported easily to any desired location of application.

A basic idea of the invention thus is that individual components of the sampler, for example the pump unit, the sensor for determining the sample amount, the control unit, the power supplying unit, or other components, are, on the one hand, constructed modularly and, on the other hand, each of these modules is embodied such that it, in itself, satisfies a predetermined ignition protection type, especially ignition protection type EEx 'd', ignition protection type EEx 'e', ignition protection type 'EEx ib', ignition protection type 'EEx m'. A further basic idea of the invention is, moreover, the matching of the ignition protection types of each of these modules individually optimally to the special requirements, which are placed on the particular components, especially such that, in spite of the explosion safety of the sampler, the sampler exhibits a total weight, which is as small as possible, and a total size which makes the sampler manageable manually.

BRIEF DESCRIPTION OF THE DRAWINGS

The invention will now be explained in greater detail on the basis of the accompanying drawings, the figures of which show as follows.

DESCRIPTION OF THE PREFERRED EMBODIMENTS

Figure 1:
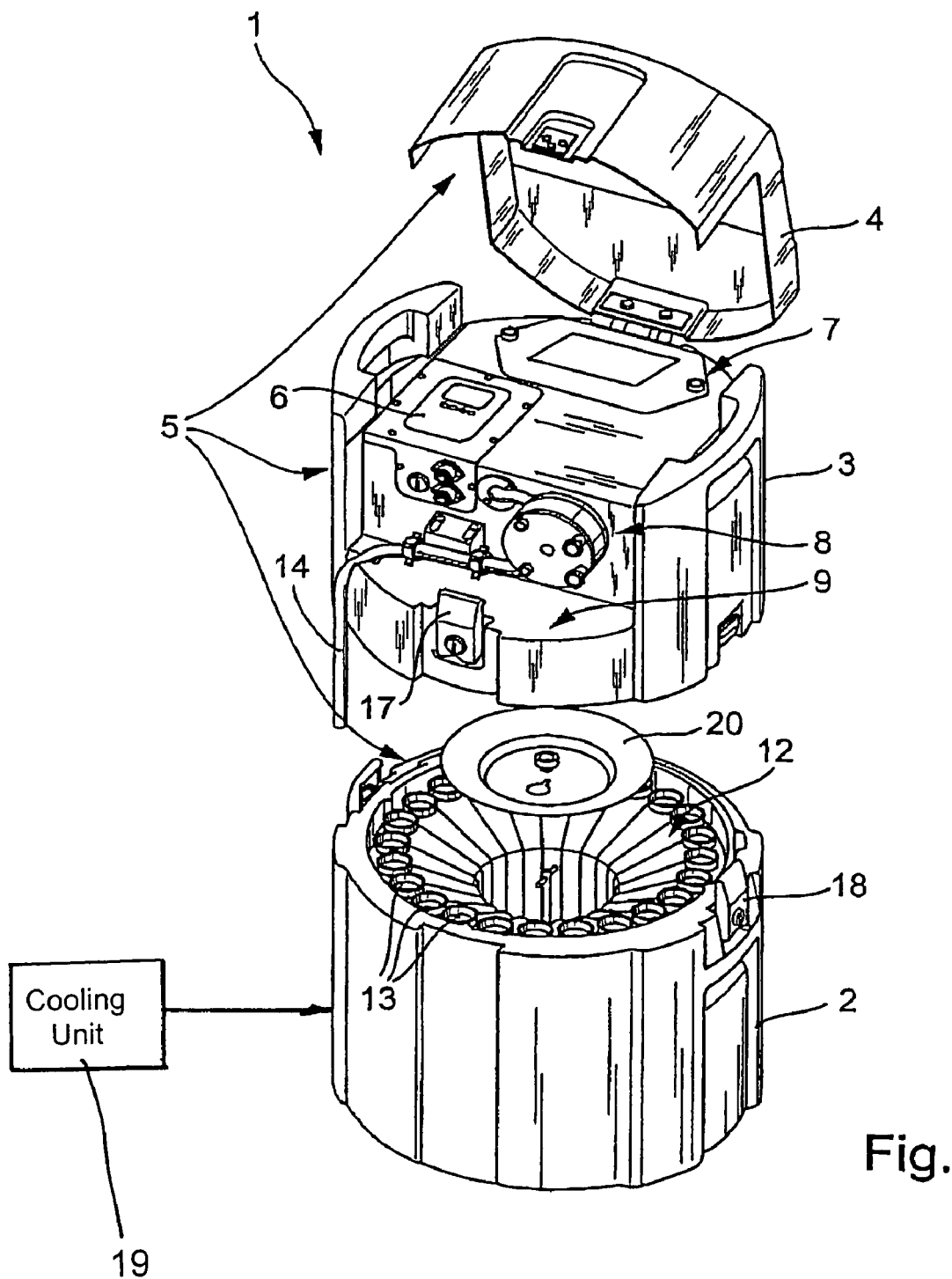
FIG. 1 a schematic representation of the sampler of the invention.

FIG. 1 is a schematic representation of the sampler 1 of the invention. The sampler 1 is constructed to be portable and serves for the discontinuous taking and storage of samples, for instance, from a sewage conduit. The sampler 1 is secured via a lockable housing 5 against unauthorized access to the taken samples.

The housing 5 of the sampler 1 comprises a lower part 2, an upper part 3 and a lid 4. The outer surface of the housing is UV-stabilized, thus resistant to UV-rays, and antistatic. Antistatic, i.e. conductive, means here that the surface resistance is smaller than 1 GΩ. This feature prevents the accumulation of an electric charge on the housing 5 of the sampler 1, which is an important prerequisite for being able to use the sampler 1 in an explosion-endangered atmosphere. Lower part 2 and upper part 3 of the housing 5 are connectable together via laterally attached locks 18. The lid 4 is securable to the upper part 3 via the lock 17. Two lateral handgrips 21 are provided on the upper part 3 to facilitate transport of the sampler 1 to its various locations of use.

In the lower part 2 of the housing 5, the sample containers 13 are arranged in the bottle distributor 12. In succession, the sample containers are filled at separate times each with a defined amount of sample taken from the location of sampling. The holddown 20 cares for fixing the sample containers 13 in the desired position.

The samples are supplied by means of the pump 8, which, in the illustrated case, is a peristaltic pump. The filled amount of sample is detected by a sensor 10. In the illustrated case, sensor 10 is a pressure sensor, which detects pressure fluctuations in line 14 and provides on the basis of these pressure fluctuations information on the amount of sample supplied through the line 14. Of course, other detection methods can be used in connection with the sampler of the invention for determining the supplied amount of sample.

In order to assure the sequentially correct filling of the sample containers 13 with the samples, a second drive unit 11 is provided. This drive 11 may be e.g. a so-called spigot drive.

The filling of the samples into the separate sample containers 13 occurs via a control unit 6. The control unit 6, that is the electronics, is located above the 'wet space' of the housing 5 accommodated in the lower part 2.

For the purpose of supplying power for the sampler 1, the invention further includes an internal power supply 7, which is, if necessary, at least temporarily fed from an external supply of energy (not shown). For example, the internal power supply unit 7 can be a rechargeable battery, which is accommodated in an appropriately provided battery compartment, especially a compartment inside housing 5.

The sampler 1 of the invention is especially suited for use in explosion-endangered areas. To support this, the sampler is constructed such that it fulfills the special safety requirements placed on devices for explosion-endangered areas. These safety requirements have the goal of avoiding a spark formation, which could possibly trigger an explosion, and/or of preventing that a spark occurring in the interior of a closed-off space of the device leads to repercussions for the surroundings. This goal is achievable in different ways, which are designated in the initially mentioned, relevant European Standards, for example, as ignition protection types. As already mentioned, comparable standards exist in the USA, Canada, Japan and other countries.

In order to enable use of the sampler in explosion-endangered areas at as small a sampler total weight as possible and with a total size which is manageable manually, the individual components 6, 7, 8, 9, 10 of the sampler are modularly constructed, with each module being so embodied that it satisfies a predetermined ignition protection type. The ignition protection types are individually optimally matched to the special requirements placed on the particular components.

In an embodiment of the invention, the sensor module 10 for detection of the supplied amount of sample is embodied such that it satisfies the ignition protection type 'EEx ib', which means that the sensor module 10 is intrinsically safe. Intrinsic safety means, in turn, that the energy required by the sensor module 10 is so small, that no spark formation can occur. Additionally, all safety-essential components of the sensor module 10 are twice, or redundantly, safeguarded.

The power supply unit 7 is designed according to one embodiment of the invention such that it satisfies ignition protection type 'EEx e', which signifies, as already explained above, an increased level of safety. On the basis of the previously named embodiments, also these components can be used in environments in which an explosive atmosphere can temporarily occur.

In a further embodiment of the sampler, there is provided on the housing 15 of the power supply unit 7 a membrane 16, which enables a gas exchange between the interior and the exterior of the housing 15. Preferably, the power supply unit 7 is a rechargeable battery. The power supply unit 7 is constructed such that it satisfies the ignition protection type 'EEx e'. Consequently, it is possible to integrate the rechargeable battery into the sampler 1. The membrane 16, which is preferably a Goretex membrane, is integrated into the lid of the battery compartment 15 and enables the required air exchange with the environment. If this air exchange could not take place, the hydrogen concentration would rise in the closed housing containing the power supply module 7, when the battery was being charged, a factor which would be a significant problem in respect to the planned location of use of the sampler 1. Preferably the power supply unit 7 involves a lead-gel, rechargeable battery, which has the advantage of being leak proof and of low maintenance. In this way, there is no need for a separate drain opening in the housing 15 of the battery.

The control unit 6 simultaneously satisfies the ignition protection types 'EEX ib' and 'EEX m'. The first named ignition protection type means that the control unit 6 is designed to be intrinsically safe; additionally, it has an encapsulation. The encapsulation is a cast encapsulation, an oil encapsulation or a sand encapsulation. Especially, casting compound is allowed to encapsulate the fuses.

As already mentioned above, the sampler 1 also has a cooling unit 19. The cooling unit 19 is preferably provided in the form of a zeolite adsorption system. This is advantageous from the point of view that a zeolite adsorption system is completely without problem as regards use in explosion-endangered areas, since it does not require any power supply.

Figure 2:
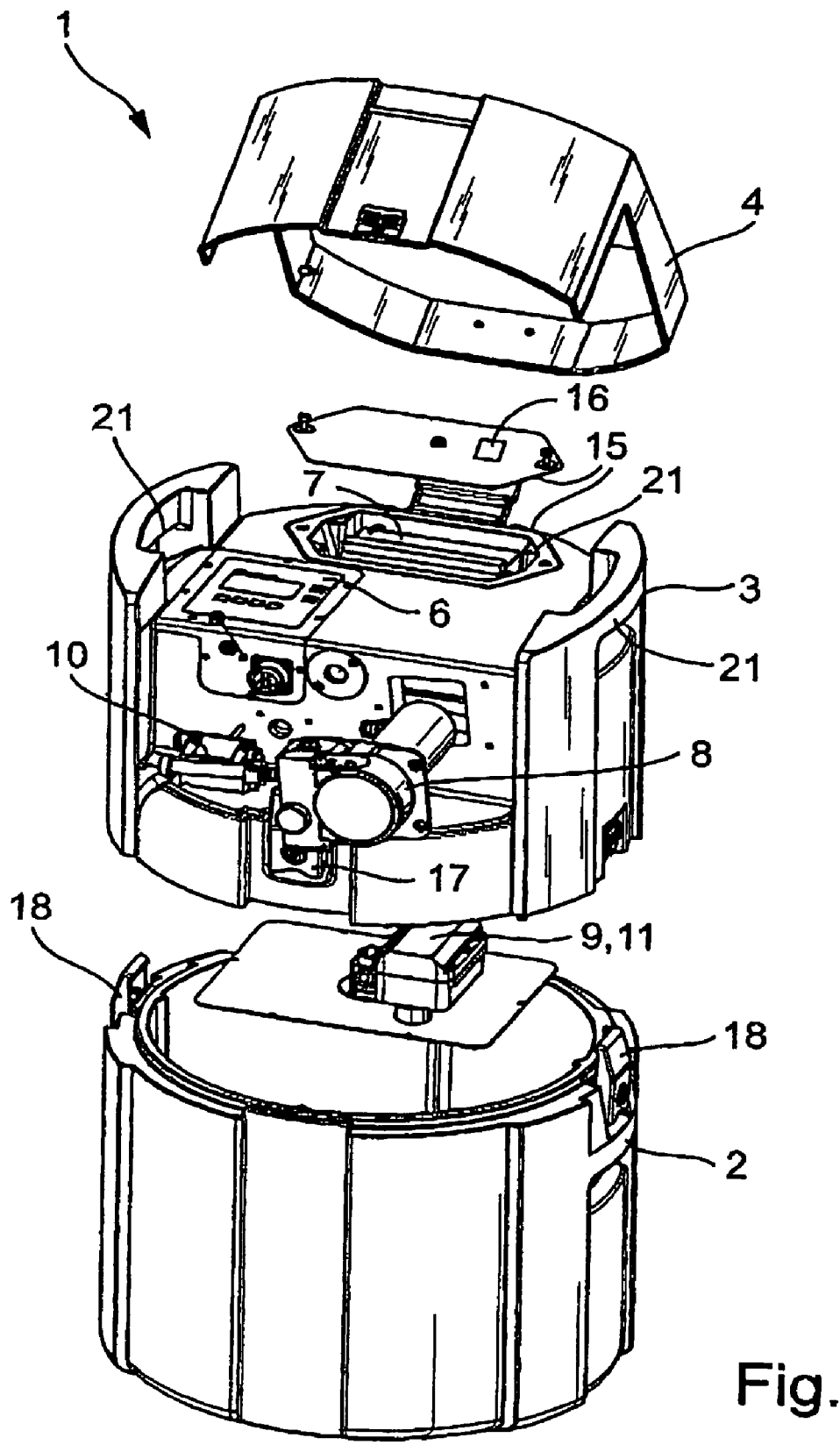
FIG. 2 an exploded view of the sampler of the invention showing the modular construction of the individual components.

FIG. 2 shows, in a generally exploded view, the essential modules, or components, 6, 7, 8, 9, 10 of the sampler 1 of the invention already described in connection with FIG. 1.

The invention claimed is:

1. A portable sampler for use in an explosion-endangered area, having a housing, in which at least the following modular components are arranged:
   a pump unit having a first drive unit;
   a sensor for determining the amount of sample supplied from said pump unit;
   a control unit, which controls the taking of a desired amount of sample and the filling thereof into at least one container; and
   at least one power supply unit, which provides the power for driving said first drive unit, said sensor and said control unit, wherein:

said control unit, said at least one power supply unit, said pump unit, and said sensor are modularly constructed, with each module having special safety requirements placed on them, said first drive unit satisfies the ignition protection type 'EExd';

said sensor satisfies the ignition protection type 'EExib';

said control unit satisfies both the ignition protection type 'EExb1' and the ignition protection type 'EExm'; and said power supply unit satisfies the ignition protection type 'EExe'.

2. The portable sampler as claimed in claim 1, wherein:
said pump unit comprises a peristaltic pump, and
said sensor is a pressure sensor, which determines the amount of sample flowing through a line of the peristaltic pump on the basis of the pressure fluctuations in the line.

3. The portable sampler as claimed in claim 1, wherein:
said power supply unit has a housing on which there is provided a membrane, which enables gas exchange between the interior and exterior of said housing of said power supply unit.

4. The portable sampler as claimed in claim 1, further having the following component:
a cooling unit, and wherein:
said cooling unit preferably comprises a zeolite adsorption system.

5. The portable sampler as claimed in claim 1, wherein:
the external surface of said housing is UV-stabilized and antistatic.

6. The portable sampler as claimed in claim 1, wherein
said first drive unit is a motor for driving a peristaltic pump.

7. The portable sampler as claimed in claim 6, further having the following components:
a second drive unit for the automatic filling of samples into a plurality of containers, wherein:
said second drive unit is modularly constructed and satisfies a specified ignition protection type.

8. A portable sampler for use in an explosion-endangered area, having a housing in which at least the following modular components are arranged:
a pump unit having a first drive unit;
a sensor for determining the amount of sample supplied from said pump unit;
a control unit, which controls the taking of a desired amount of sample and the filling thereof into at least one container; and
at least one power supply unit for driving said first drive unit, said sensor and said control unit, wherein:

said control unit, said at least one power supply unit and said sensor are modularly constructed, with each module having special safety requirements placed on them, wherein said first drive unit is encapsulated in a pressure-tight manner;

energy supplied to said sensor is not sufficient for spark formation;

energy supplied to said control unit is not sufficient for spark, formation and said control unit has an encapsulation; and said power supply has a housing comprising a membrane, which enables gas exchange between the interior and the exterior of the housing.

9. The portable sampler as claimed in claim 8, wherein said first drive unit is a motor for driving a peristaltic pump.

10. The portable sampler as claimed in claim 8, further having the following components:
a second drive unit for the automatic filling of samples into a plurality of containers, wherein:
said second drive unit is modularly constructed and is encapsulated in a gas tight manner.

11. The portable sampler as claimed in claim 8, wherein:
said pump unit comprises a peristaltic pump, and
said sensor is a pressure sensor, which determines the amount of sample flowing through a line of the peristaltic pump on the basis of the pressure fluctuations in the line.

12. The portable sampler as claimed in claim 8, further having the following component:
a cooling unit, and wherein:
said cooling unit comprises a zeolite adsorption system.

13. The portable sampler as claimed in claim 8 wherein said encapsulation of said control unit comprises a cast encapsulation, an oil encapsulation or a sand encapsulation.

* * * * *